US 6,563,653 B2

(12) United States Patent
Ramm et al.

(10) Patent No.: US 6,563,653 B2
(45) Date of Patent: May 13, 2003

(54) DIGITAL IMAGING SYSTEM FOR ASSAYS IN WELL PLATES, GELS AND BLOTS

(75) Inventors: Peter Ramm, St. Catharines (CA); Gang Sun, St. Catharines (CA); Rolf Mueller, Auburn, NY (US); Timothy Ormsby, Auburn, NY (US); Kenneth R. Castle, Tucson, AZ (US)

(73) Assignee: Imaging Research, Inc., St. Catharines (CA)

( * ) Notice: Subject to any disclaimer, the term of this patent is extended or adjusted under 35 U.S.C. 154(b) by 0 days.

(21) Appl. No.: 10/138,764

(22) Filed: May 3, 2002

(65) Prior Publication Data

US 2002/0159162 A1 Oct. 31, 2002

Related U.S. Application Data

(62) Division of application No. 09/240,649, filed on Jan. 29, 1999, now Pat. No. 6,441,973, which is a continuation of application No. PCT/US97/15269, filed on Aug. 12, 1997.
(60) Provisional application No. 60/024,043, filed on Aug. 16, 1996.

(51) Int. Cl.[7] .......................... G02B 9/36; G02B 13/22; C12Q 1/68; A61K 31/70

(52) U.S. Cl. .................. 359/778; 359/663; 435/6; 514/44
(58) Field of Search .................. 359/663, 778, 359/634; 435/6; 514/44

(56) References Cited

U.S. PATENT DOCUMENTS

RE36,560 E * 2/2000 Svetkoff et al. ............ 356/376
6,258,325 B1 * 7/2001 Sanadi ....................... 422/101

* cited by examiner

Primary Examiner—Georgia Epps
Assistant Examiner—Timothy Thompson
(74) Attorney, Agent, or Firm—Darby & Darby

(57) ABSTRACT

An electronic imaging system is disclosed, for assessing the intensity of colorimetric, fluorescent or luminescent signal in a matrix consisting of wells, microwells, hybridization dot blots on membranes, gels, or other specimens. The system includes a very sensitive area CCD detector, a fast, telecentric lens with epi-illumination, a reflective/transmissive illumination system, an illumination wavelength selection device, and a light-tight chamber. A computer and image analysis software are used to control the hardware, correct and calibrate the images, and detect and quantify targets within the images.

5 Claims, 9 Drawing Sheets

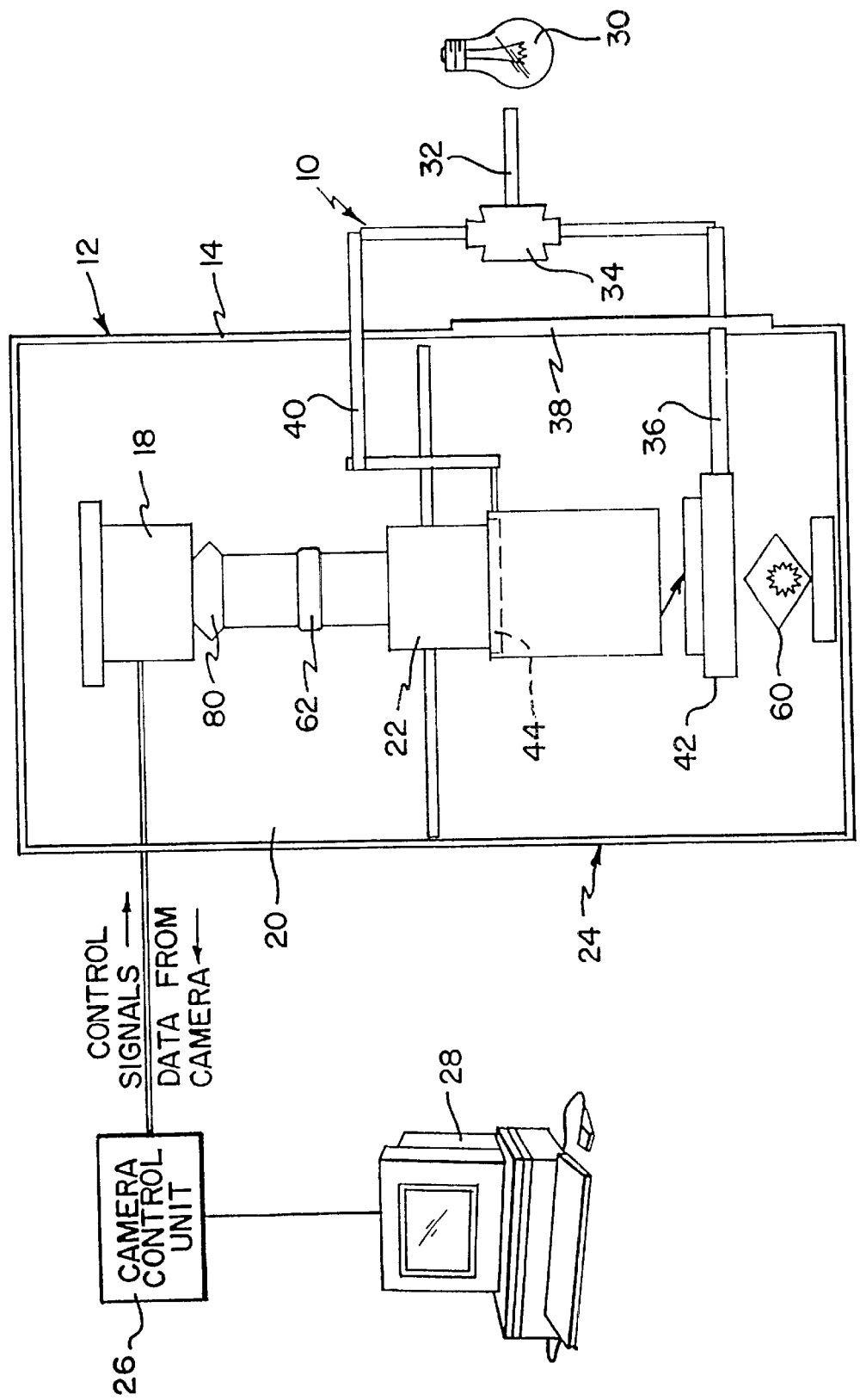

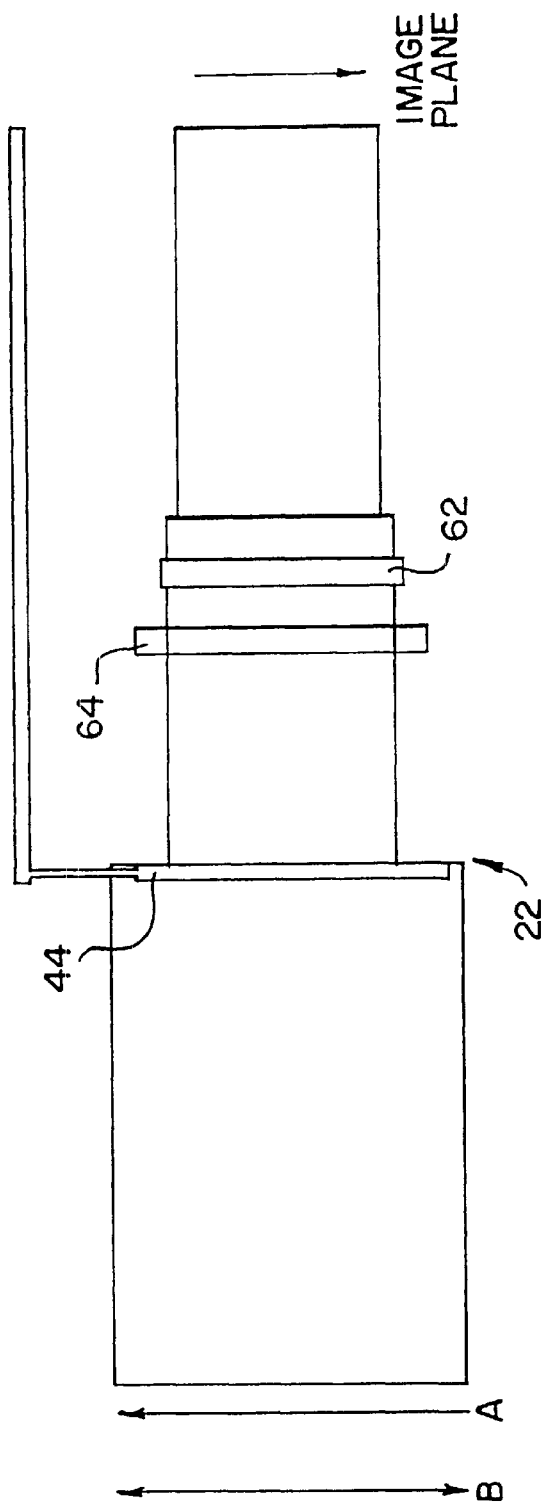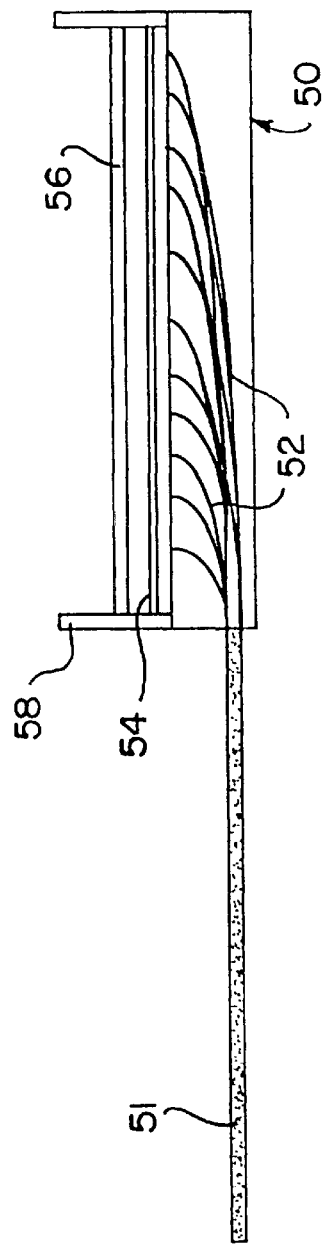

DIGITAL IMAGING SYSTEM FOR ASSAYS IN WELL PLATES, GELS AND BLOTS

This patent application claims the priority of U.S. Provisional Application No. 60/024,043 filed Aug. 16, 1996. This is a division, of application Ser. No. 09/240,649 filed Jan. 29, 1999, now U.S. Pat. No. 6,441,973, which is a continuation of International Application No. PCT/US97/15269, filed Aug. 12, 1997, which was published in English. Each of these prior applications is hereby incorporated herein by reference, in its entirety.

FIELD OF THE INVENTION

The present invention relates generally to assay analyzing systems and, more particularly, concerns a system and method for creating digital images of randomly arranged specimens (e.g. beads within gels, colonies within petri dishes) or specimens arranged in regular arrays (e.g. wells in plastic plates, dots spotted onto membranes). The invention is capable of creating digital images and performing automated analyses of specimens which emit very low levels of fluorescence, chemiluminescence, or bioluminescence. More particularly, the invention is designed for the analysis of luminance arising from assays within well plates and gel media, and on membranes, glass, microfabricated devices, or other supports.

BACKGROUND OF THE INVENTION

Types of Assays

Many chemical and molecular biological assays are designed so that changes in the absorbance, transmission, or emission of light reflect reactions within the specimen. Therefore, instruments used to quantify these assays must detect alterations in luminance.

Wells. Some assays are conducted within discrete flasks or vials, while others are performed within plastic plates fabricated to contain a number of regularly spaced wells. "Well plate" assays are higher in throughput and lower in cost than similar assays in discrete containers. Standard well plates contain 96 wells in an area of 8×12 cm. The trend is to higher numbers of wells, within the same plate size. Today's highest commercial density is 384 wells. Very high density arrays of small wells (microwells, e.g. thousands/plate with a fill volume of less than 1 ul/well) are under development, and will become commercially available as microwell filling and detection technologies mature.

Dot blots. Grids of small dots (reactive sites) are placed onto flat support membranes or slips of treated glass. A high density grid can contain many thousands of discrete dots. Grid assays usually involve hybridization with synthetic oligonucleotides, to look for genes containing specific sequences, or to determine the degree to which a particular gene is active. Applications include library screening, sequencing by hybridization, diagnosis by hybridization, and studies of gene expression. High density grids provide the potential for very high throughput at low cost, if analyzing the grids can be made simple and reliable. Therefore, considerable commercial attention is directed at companies developing technology for creating, detecting, and analyzing high density arrays of genomic sequences.

Combinatorial assays. Some assays involve small particles (typically beads coated with compounds) which act as the reactive sites. There might be many thousands of beads, each coated with a different compound (e.g. molecular variants of an enzyme) from a combinatorial library. These beads are exposed to a substance of interest (e.g. a cloned receptor) in wells, or in a gel matrix. The beads which interact with the target substance are identified by fluorescence emission or absorption in the region around each bead. Beads which interact are surrounded by faint areas of altered luminance. Very sensitive detectors are required to identify the subtle alterations in luminance around the beads that interact with the target.

Electrophoretic separations. A solubilized sample is applied to a matrix, and an electrical potential is applied across the matrix. Because proteins or nucleic acids with different amino acid or nucleotide sequences each have a characteristic electrostatic charge and molecular size, components within the sample are separated by differences in the movement velocities with which they respond to the potential. The separated components are visualized using isotopic, fluorescent, or luminescent labels. In many cases (e.g. chemiluminescence), the luminance from the specimen is very dim.

Assays which occur within a regularly spaced array of active sites (wells, dot blots within a grid) can be referred to as fixed format assays. Assays which involve specimens that are irregularly distributed within a gel or blot matrix can be termed free format assays.

Fixed format assays are usually performed without imaging. In contrast, free format assays require the use of image analysis systems which can detect and quantify reactions at any position within an image.

Instruments designed for fixed format assays generally lack imaging capabilities, and have not been applied to free formats. Similarly, very few imaging instruments designed for free formats have been applied to wells, and other fixed format targets.

Nonimaging Counting Systems

Nonimaging counting systems (liquid scintillation counters, luminometers, fluorescence polarization instruments, etc.) are essentially light meters. They use photomultipliers (PMTs) or light sensing diodes to detect alterations in the transmission or emission of light within wells. Like a light meter, these systems integrate the light output from each well into a single data point. They provide no information about spatial variations within the well, nor do they allow for variation in the packing density or positioning of active sites.

Each PMT reads one well at a time, and only a limited number of PMTs can be built into a counting system (12 is the maximum in existing counting systems). Though the limited number of PMTs means that a only few wells are read at a time, an array of wells can be analyzed by moving the PMT detector assembly many times.

The major advantages of nonimaging counting systems are that they are a "push-button" technology (easy to use), and that the technology is mature. Therefore, many such instruments are commercially available, and their performance is well-characterized.

The major disadvantages of counting systems are:
a. Limited flexibility—few instruments can cope with 384 wells, and higher density arrays of fluorescent or luminescent specimens are out of the question.
b. Fixed format only—designed as well or vial readers, and cannot read specimens in free format.
c. Slow with dim assays—although scanning a few wells at a time can be very fast when light is plentiful, dim assays require longer counting times at each position within the scan. As there are many positions to be scanned, this can decrease throughput.

In summary, non-imaging counting systems are inflexible and offer limited throughput with some specimens.

Scanning Imagers

For flat specimens, an alternative to nonimaging counting is a scanning imager. Scanning imagers, such as the Molecular Dynamics (MD) Storm, MD FluorImager, or Hitachi FMBIO pass a laser or other light beam over the specimen, to excite fluorescence or reflectance in a point-by-point or line-by-line fashion. Confocal optics can be used to minimize out of focus fluorescence (e.g. the Biomedical Photometrics MACROscope), at a sacrifice in speed and sensitivity. With all of these devices, an image is constructed over time by accumulating the points or lines in serial fashion.

Scanning imagers are usually applied to gels and blots, where they offer convenient operation. A specimen is inserted and, with minimal user interaction (there is no focusing, adjusting of illumination, etc.), the scan proceeds and an image is available. Like the nonimaging counting system, the scanning imager is usually a push-button technology. This ease of use and reasonably good performance has lead to an increasing acceptance of scanning imagers in gel and blot analyses.

Scanning imagers have four major shortcomings:

a. Slow scanning. The beam and detector assembly must be passed over the entire specimen, reading data at each point in the scan. Scanning a small specimen could easily take 5–10 minutes. A large specimen might take ½ hour to scan. This slow scan limits throughput, and complicates the quantification of assays that change during the scan process.

b. Limited number of wavelengths. A limited number of fluorescence excitation wavelengths is provided by the optics. Therefore, only a limited number of assay methods can be used.

c. Low sensitivity. Most scanning imagers exhibit lower sensitivity than a state of the art area imager.

d. Not appropriate for luminescence. Scanning imagers require a bright signal, resulting from the application of a beam of light to the specimen. Therefore, specimens emitting dim endogenous luminescence (e.g. reactions involving luciferase or luminol) cannot be imaged.

e. Not appropriate for wells. Only flat specimens can be imaged. A limited number of confocal instruments can perform optical sectioning and then reconstruct the sections into a focused thick image.

Area Imaging

An area imaging system places the entire specimen onto a detector plane at one time. There is no need to move PMTs or to scan a laser, because the camera images the entire specimen onto many small detector elements (usually CCDs), in parallel. The parallel acquisition phase is followed by a reading out of the entire image from the detector. Readout is a serial process, but is relatively fast, with rates ranging from thousands to millions of pixels/second.

Area imaging systems offer some very attractive potential advantages.

a. Because the entire specimen is imaged at once, the detection process can be very quick.

b. Given an appropriate illumination system, any excitation wavelength can be applied.

c. Luminescence reactions (emitting light without incident illumination) can be imaged, including both flash and glow bioluminescence or chemiluminescence.

d. Free or fixed format specimens can be imaged.

Luminescence imaging is more easily implemented, in that illumination does not have to be applied. However, most luminescence reactions are quite dim, and this can make extreme demands upon existing area imaging technology. The standard strategy is to use sensitive, cooled scientific grade CCD cameras for these types of specimens. However, in the absence of the present invention, integrating cameras will fail to image many luminescent specimens. Therefore, the present invention can image specimens that other systems cannot.

Typical prior art systems apply area imaging to luminescent assays on flat membranes and luminescent assays in wells. Standard camera lenses are always used. The results of well imaging are flawed, in that there is no correction for parallax error.

There is more extensive prior art regarding use of area imaging in fluorescence. Fluorescence microscopy (see Brooker et al. U.S. Pat. No. 5,332,905) and routine gel/blot imaging are the most common applications. Prior art in microscopy has little relevance, as no provision is made for imaging large specimen areas.

The existing art relating to macro specimens is dominated by low cost commercial systems for routine gel/blot fluorescence. These systems can image large, bright areas using standard integrating CCD cameras. However, they have major disadvantages:

a. Limited to the wavelengths emitted by gas discharge lamps. Typically some combination of UVA, UVB, UVC, and/or white light lamps is provided. Other wavelengths cannot be obtained.

b. Wavelengths cannot be altered during an assay. If the illumination must be changed during the assay (e.g. as for calcium measurement with fura-2), the devices cannot be adapted.

c. Insensitive to small alterations in fluorescence. Transillumination comes from directly below the specimen into the detector optics. Therefore, even very good filters fail to remove all of the direct illumination, and this creates a high background of nonspecific illumination. Small alterations in fluorescence (typical of many assays) are lost within the nonspecific background.

d. Inefficient cameras and lenses. A very few systems use high-performance cameras. Even these few systems use standard CCTV or photographic lenses, which limit their application to bright specimens.

e. Parallax error precludes accurate well imaging. As fast, telecentric lenses have not been available, these systems exhibit parallax error when imaging wells.

Novel features of the present invention minimize the disadvantages of known macro fluorescence systems. These novel features include:

a. Illumination wavelengths may be selected without regard to the peak(s) of a gas discharge lamp or laser.

b. Using a computer-controlled filter wheel or other device, illumination may be altered during an assay, c. Small alterations in fluorescence emission can be detected. Because fluorescence illumination comes via epi-illumination, or from a dorsal or lateral source, direct excitation illumination does not enter the optics. This renders the nonspecific background as low as possible.

d. Very efficient camera and lens system allow use with dim specimens.

e. Unique telecentric lens is both very fast, and removes parallax error so well plate assays are accurate.

A primary advantage of the present invention is its fast, telecentric lens, which can image an entire well plate at once, and which can provide efficient epi-illumination to transparent or opaque specimens. Fiber optic coupling to the specimen can be used instead of lens coupling. For example, a fiber optic lens has been used with an image intensified CCD camera run in photon counting mode for analyses of data in fixed or free formats. This approach yields good sensitivity, but has the following major disadvantages:

a. Although it is suggested that the system could be used with fluorescent specimens, it would be limited to specimens that are transilluminated, because there is no place to insert an epi-illumination mechanism. Therefore, the fiber lens system would have degraded sensitivity, and could not be used with opaque specimens. Many specimens are opaque (e.g. many well plates, nylon membranes).

b. Well plates are 8×12 cm. Image forming fiber optics of this size are very difficult and expensive to construct. Therefore, the specimen would have to be acquired as a number of small images, which would then be reassembled to show the entire specimen.

This multiple acquisition would preclude use of the device with assays which change over time.

An area imaging analysis system (LUANA) is disclosed by D. Neri et al. ("Multipurpose High Sensitivity Luminescence Analyzer", Biotechniques 20:708–713, 1996), which uses a cooled CCD, side-mounted fiber optic illuminator, and an excitation filter wheel to achieve some functions similar to the present invention (selection of wavelengths, area imaging). However, LUANA uses a side-mounted fiber optic, which is widely used in laboratory-built systems, and creates problems that are overcome by the present invention. Specifically, use of a side-mounted fiber optic provides very uneven illumination, particularly when used with wells. The epi- and transillumination systems of the present invention provide even illumination of both flat specimens and wells. Further, in LUANA, parallax would preclude imaging of assays in wells.

Another system (Fluorescence Imaging Plate Reader—FLIPR of NovelTech Inc., Ann Arbor Mich.) uses an area CCD to detect fluorescence within 96 well plates. This device is a nonimaging counting system, and uses the area CCD instead of multiple PMTs. To achieve reasonable sensitivity, it runs in 96 well format and bins all pixels within each well into a single value. The device is not applicable to luminescence imaging, free format imaging, or higher density well formulations and is very costly.

There is extensive prior art in the use of imaging to detect assays incorporated within microfabricated devices (e.g. "genosensors"). Some genosensors use scanning imagers, and detect emitted light with a scanning photomultiplier. Others use area CCDs to detect alterations at assay sites fabricated directly onto the CCD, or onto a coverslip that can be placed on the CCD. Genosensors have great potential when fixed targets are defined. For example, a chip is fabricated that looks for a specific sequence of genomic information, and this chip is used to screen large numbers of blood samples. While highly efficient for its designed sequence, the chip has to contain a great number of active sites if it is to be useful for screening a variety of sequences. Fabrication of chips with many thousands of sites is costly and difficult. Therefore, the first generation of genosensors will be applied to screening for very specific sequences of nucleotides.

The inflexibility of the microfabricated device contrasts with the present invention, which does not require microfabrication of the assay substrate. Instead, the present invention permits assays to be conducted in wells, membranes, silicalized slides, or other environments. Almost any reaction may be quantified. Thus, the present invention could be used as an alternative technology to microfabrication. Because the present invention is flexible, and allows almost any chemistry to be assayed, it can be used for all phases of assay development. These include prototyping, and mass screening. The invention therefore provides an alternative to microfabrication, when microfabrication is not feasible or cost-effective.

Each of the prior art references discussed above treats some aspect of imaging assays. However, the prior art does not address all of the major problems in imaging large specimens at low light levels. The major problems in low light, macro imaging are:

a. very high detector sensitivity required;

b. flexible, monochromatic illumination of large areas is required;

c. parallax error must be avoided; and d. more reliable procedures are needed to find and quantify targets.

Broadly, it is an object of the present invention to provide an imaging system for assays which overcomes the shortcomings of prior art systems. It is specifically intended to provide a complete system for the area imaging of assays in wells and on membranes. It is specifically contemplated that the invention provide a complete system for the area imaging of chemiluminescent, fluorescent, chemifluorescent, bioluminescent, or other nonisotopic hybridization assays, including high density dot blot arrays.

It is another object of the invention to image chemiluminescent, fluorescent, chemifluorescent, bioluminescent, or other nonisotopic assays, including combinatorial assays, in free format.

It is an object of the invention to provide software for digital deconvolution of the fluorescence image data. Application of the software decreases flare and out of focus information.

It is also an object of the present invention to provide a method and system for imaging assays which are flexible, reliable and efficient in use, particularly with low level emissions.

The present invention provides synergistic combination of detector, lens, imaging system, and illumination technologies which makes it able to image the types of specimens previously acquired with nonimaging counters and scanning imagers. In particular, it can be used with fixed or free formats, and with wells or flat specimens. It is able to detect fluorescence, luminescence, or transmission of light.

The features of the invention include that it detects and quantifies large arrays of regularly spaced targets, that it detects and quantifies targets that are not arranged in regular arrays, and that it performs automated analyses of any number of regularly spaced specimens, from small numbers of large wells to large numbers of very small wells or dot blots.

It is another feature of the invention to provide an area illumination system that: can deliver homogenous monochromatic excitation to an entire well plate or similarly sized specimen, using standard and low cost interference filters to select the excitation wavelength; and can deliver varying wavelengths of homogenous monochromatic excitation to an entire well plate or similarly sized specimen, under computer control.

A system embodying the invention provides a lens designed specifically for assays in the well plate format. This lens is very efficient at transferring photons from the specimen to the CCD array (is fast), preferably contains an epi-illumination system, and can be used with very dim specimens. The lens is also telecentric. A telecentric lens has the property that it peers directly into all points within a well plate, and does not exhibit the parallax error that is characteristic of standard lenses.

A preferred system provides a telecentric and fast lens that generates an even field of epi-illumination, when required. The lens is equipped with an internal fiber optic illumination system, that does not require a dichroic mirror. Preferably, the lens is constructed to accept an internal interference filter used as a barrier filter. Light rays passing through the lens are almost parallel when they strike the barrier filter, so that the filter operates at its specified wavelength and bandwidth tolerance.

It is a feature of the invention that it provides high light gathering efficiency, whether used with a fast telecenric lens, or standard photographic lenses.

A preferred system provides a CCD area array camera that has high quantum efficiency (approximately 80%), and high-sensitivity (16 bit precision), so that most specimens can be detected by integration without intensification. Preferably, the system has an integrating, cooled CCD camera which has coupled thereto an optional image intensifier. In an embodiment intended for extremely low light levels, incident illumination from the specimen is amplified by the intensifier, and the amplified light is accumulated onto the integrating camera over an integration period. At the end of the integration period, the camera is read out to a dedicated controller or imaging apparatus to reproduce the light image. Multiple exposures may be used to increase the dynamic range of the camera. A light-tight specimen chamber is provided, to which all illumination and detection components may be mounted, and which contains the specimens.

A system in accordance with the invention may incorporate a translation stage (optional), that may be housed within the light-tight chamber and used to move large specimens (e.g. 22×22 cm membranes) past the optical system. The invention controls the stage motion through software, and that creates a single composite image from the multiple "tiles" acquired with the translation stage.

Preferably, the invention provides software control that corrects the shading, geometric distortion, defocus, and noise errors inherent to the camera and lens system; and that removes as much nonspecific fluorescence as possible, using multiple images created with different excitation filters.

In particular, the invention provides software to deconvolve images from a single focal plane, using optical characteristics previously measured from the lens and detector system. It should be appreciated that data from multiple focal planes may also be deconvolved.

While the preferred embodiment of the invention uses a high-precision, cooled CCD camera, if cost is a major factor, the present invention could be constructed using lower cost integrating cameras. In this case, shorter integration periods can be achieved, with a reduction in image quality and ultimate sensitivity.

BRIEF DESCRIPTION OF THE DRAWINGS

Further objects, features and advantages of the invention will be understood more completely from the following detailed description of a presently preferred, but nonetheless illustrative embodiment, with reference being had to the accompanying drawings, in which:

FIG. 1 is a schematic illustration of a system in accordance with a first preferred embodiment (upright) of the invention;

FIG. 2 is a schematic illustration, in side view, of the fast, telecentric lens;

FIG. 6 is a schematic illustration of the diffuse illumination plate in side view, showing how discrete fiber bundles from the main bundle are taken to locations within the rectangular fiber holder;

DETAILED DESCRIPTION OF THE PREFERRED EMBODIMENTS

Figure 3:
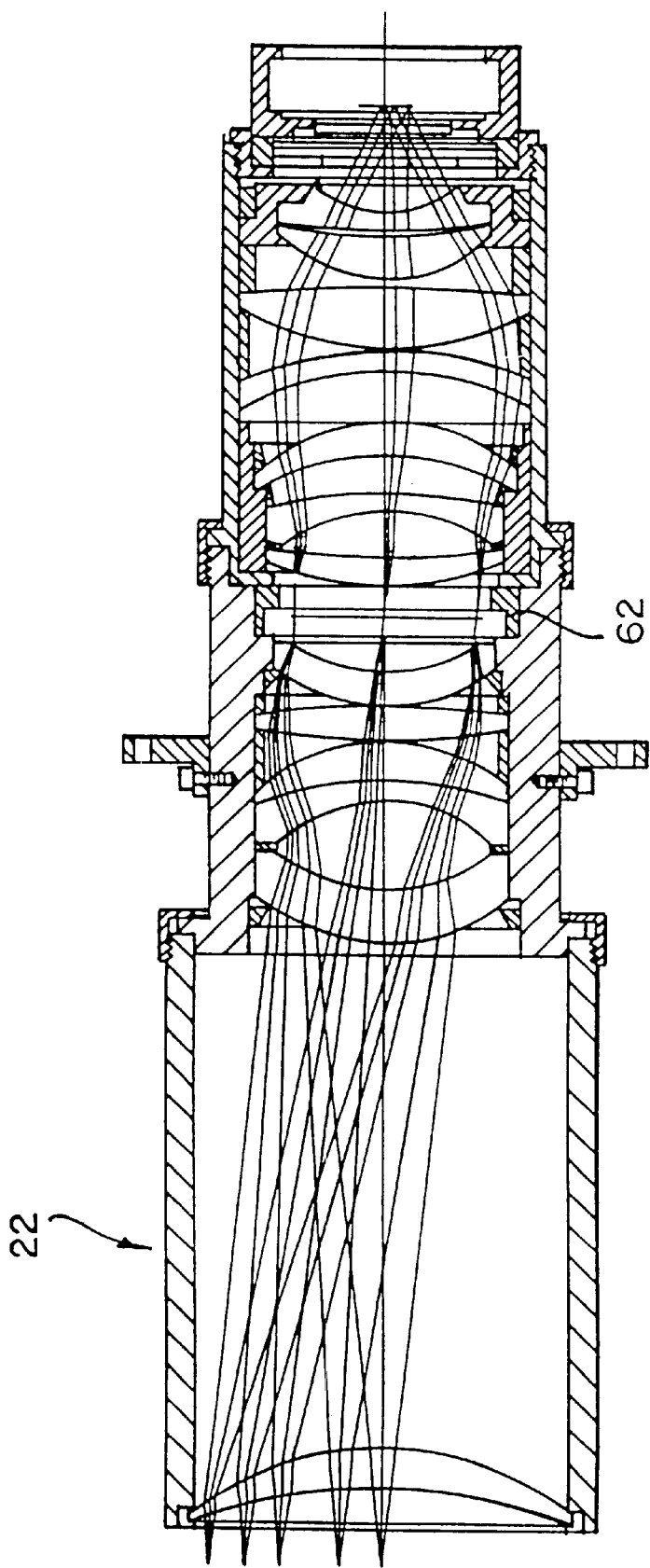
FIG. 3 is a detailed illustration of the optical and mechanical components of the lens and the emission filter holder.

Turning now to the details of the drawings, FIG. 1 is a schematic diagram illustrating a preferred embodiment of an imaging system 1 in accordance with the present invention. System 1 broadly comprises an illumination subsystem 10, an imaging subsystem 12 provided in an housing 14, and a control subsystem 16. The imaging subsystem 12 comprises a CCD camera subsystem 18 housed within a camera chamber 20 of housing 14 and a lens subassembly 22 extending between camera chamber 20 and a specimen chamber 24. In operation, illumination subsystem 10 provides the necessary light energy to be applied to the specimen within chamber 24. Light energy emitted by the specimen is transmitted through lens subsystem 22 to camera 18, where an image is formed and transmitted to the control subsystem 16 for processing. Control subsystem 16 comprises a camera control unit 26, which is a conventional unit matched to the particular camera 18 and a computer 28 which is programmed to control unit 26 and to receive data from camera 18, in order to achieve unique control and processing in accordance with the present invention.

The light source for the illumination subsystem 10 is preferably an arc lamp 30. Light from lamp 30 is conducted via a liquid light guide 32 to the optical coupler or filter wheel 34. The liquid light guide 32 is advantageous in that it transmits in the UV range, and in that it acts to diffuse the input illumination more than a fiber optic would do.

The optical coupler 34 contains a conventional filter holder (not shown) for standard, one inch diameter interference filters. In the preferred configuration, a computer controlled filter wheel is used instead of the optical coupler. The filter wheel can contain a number of filters, which can be rapidly changed under computer direction.

A fiber optic bundle 36 carries illumination from the optic coupler or filter wheel 34 to within the light-tight specimen chamber 24. The bundle 36 passes through a baffle 38, which allows it to move up and down during focusing of the specimen holder. Alternatively, the fiber optic bundle 40 from the epi-illumination ring light in lens 22 may be connected to the optical coupler 34.

Three forms of illumination system are described, each fed by a discrete fiber bundle. These are a transilluminating plate (42), a ring light external to the lens (not shown), and a ring light 44 internal to the lens (22) that performs epi-illumination.

Figure 7:
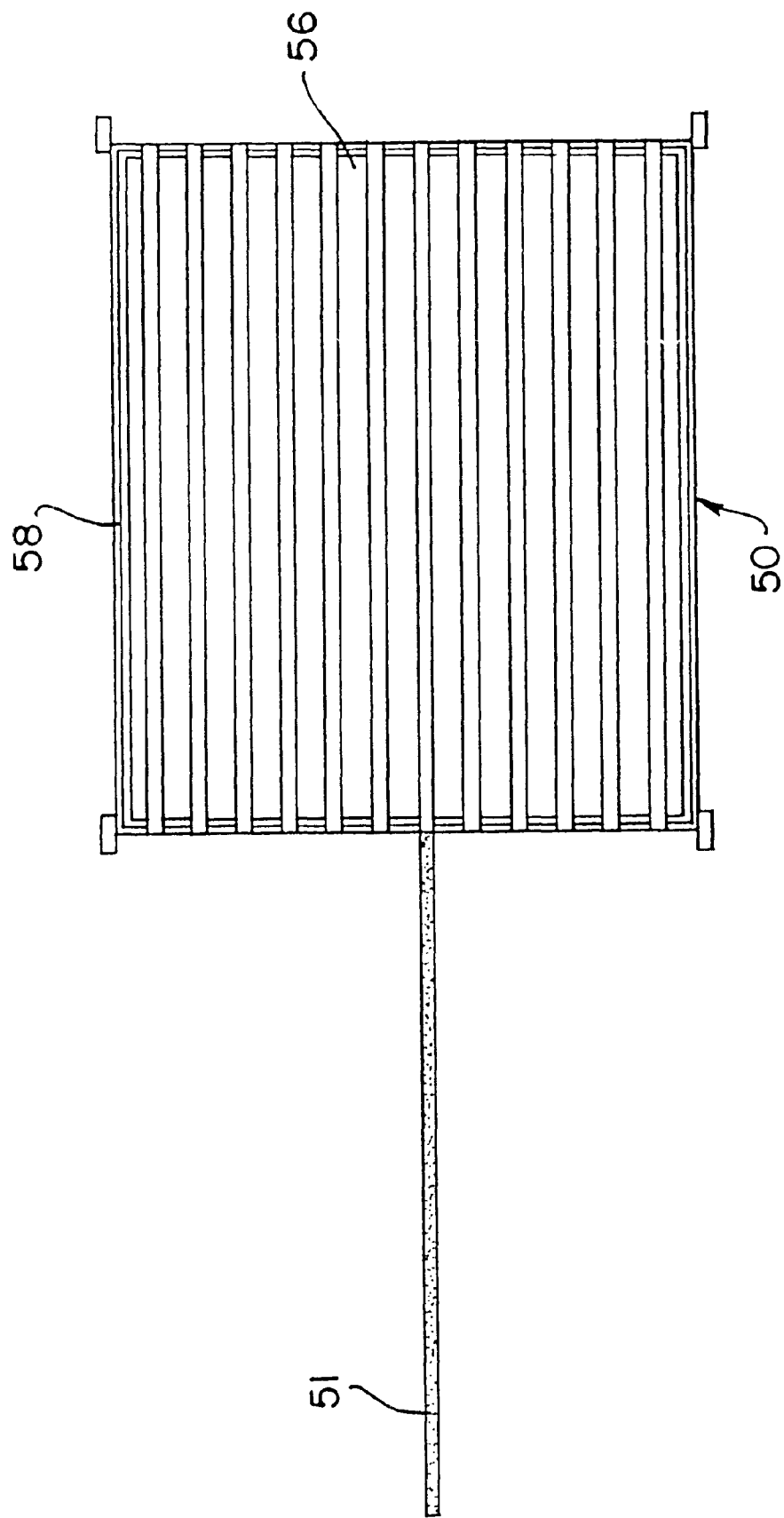
FIG. 7 is a schematic illustration of the diffuse illumination plate in top view, showing how discrete fiber bundles from the main bundle are taken to an array of channels within the fiber holder.

The transillumination plate is a rectangular chamber 50 (see FIGS. 6 and 7), within which the discrete fibers 52 from bundle 51 are separated and rotated by 90 degrees so that they point laterally, towards the specimen. The fibers 52 are distributed within the chamber in such a way that they minimize shading within the illumination pattern. To this end, a larger number of fibers lie in the peripherally outward portions of the chamber than lie at its center.

The rectangular chamber 50 contains a diffusing screen 54, and a quartz glass diffusing plate 56. These diffusing elements take as their input the discrete points of light from the fibers 52, and create a homogenous illumination over the surface of the plate 56. The chamber 50 may also contain a dark field stop, to allow light to enter the specimen from the side.

The external ring light consists of a ring of optical fibers aligned with the axis of the lens, with a hole in the center large enough to encircle the lens 22. The working distance of the ring light is matched to the focus distance of the lens 22.

The internal ring light 44 consists of a ring of optical fibers, mounted within and axially aligned with the body of the telecentric lens 22, and behind its front lens element. A diffuser, polarizer, or other circular element may be placed at the front of the fiber ring 44.

The specimen well plate is carried within a holder 58 (FIG. 6) that is mounted to the fiber optic chamber 50. The holder 58 grips the well plate at its edges. The bottom of the holder 58 is empty, so as not to impede viewing of the wells. The holder 58 is mounted to a jack, which moves it in the vertical dimension. By adjusting the jack 60, the holder 58 moves relative to the lens 22 and the specimen is focused.

The lens 22 is a fast, telecentric lens. The lens contains an emission filter slot 62, which accepts three inch diameter interference filters for fluorescence imaging. It contains an internal fiber optic ring light 44, positioned behind the front lens element. The lens 22 is mounted to the camera chamber by a flange 64 (see FIG. 2) at its middle. The back of the lens projects into the camera chamber 20, providing ready access to the emission filter slot 62 without disturbing the specimen. The front of the lens projects into the specimen chamber 24.

The cooled CCD camera 18 is mounted directly to the lens. Because the camera has its own chamber 20, there is no need for concern regarding light leakage around the cooling, power and data cables that exit the chamber to the camera control unit.

All control, imaging, and analysis functions are resident within the computer 28.

Illumination Subsystem

The standard technology for monochromatic area illumination is to use gas discharge illuminators (e.g. UV light boxes), which can deliver about 5000 uW/cm$^2$ of surface at the emission peaks (usually mercury). The lamps are coated with a filter that limits emission to a specific peak. Although fairly bright, gas discharge lamps are limited in wavelength to the peaks emitted by the excited gas within the lamp.

Other than gas discharge lamps, very few descriptions of area illumination exist. The major problems are selection of wavelength, and that direct entrance of the illuminating beam into the collection optics degrades sensitivity. To avoid this, light can be delivered from above, from the side, or via dark field or refraction into the specimen. All of these techniques have severe limitations. Side-mounted fiber optic illuminators are uneven. They are also unsuited to wells or other non-flat specimens, because light enters the specimen at an angle and fails to penetrate deep targets. Refractive or dark field illuminators require special optical components at the well plate, and cannot be used with opaque specimens.

A more flexible area illumination system would use a broad-band illumination source, and would allow any wavelength of monochromatic illumination to be selected by precision filters (usually interference filters). Filters are preferred, because variable monochromators or low cost tunable lasers lack sufficient light output when diffused over large areas.

Mercury or xenon arc lamps are often selected for filter-based monochromatic excitation. The advantage of an arc lamp is that its output can be made into a narrow beam that can be passed through a small and readily available interference filter, before being spread over the entire surface of the specimen. Either a lens or fiber optic may be used to transmit the monochromatic light from the filter to the specimen.

The present invention is much more flexible than any previous device. It applies diffuse transillumination (through the specimen), dorsal illumination (via ring light or other source), or epi-illumination (through the lens) to the entire surface of the specimen. Epi-illumination is preferred, because it usually results in lower backgrounds, broader dynamic range, and more linear fluorescence response under real-world conditions. The ability to deliver large area monochromatic epi-illumination is one critical factor that sets the present invention apart from prior art.

The present invention addresses three main problems in illumination delivery.

a. Filter availability—Close-tolerance filters (e.g. a 10 nm bandwidth filter), which are readily available in small sizes, are not available for large areas of illumination. This problem is overcome by use of standard interference filters.

b. Illumination delivery—Application of even, monochromatic, and selectable illumination over an 8×12 cm area is a feature of the present invention. An optical coupler or computer-controlled filter wheel accepts standard interference filters, and is used to select wavelengths. The optical coupler or wheel may be attached to a specially designed fiber optic plate for transillumination, to a fiber optic ring or panel light for dorsal illumination, or to a fiber optic illumination assembly within the lens, for epi-illumination.

c. Intensity—The excitation illumination is spread over a large area (typically 96 cm$^2$). As intensity decreases with the square of the illuminated area, the resulting excitation intensity is very low indeed. In many cases, emitted fluorescence will not be detected with standard, scientific-grade cooled CCD cameras. The very sensitive detector of the present invention is capable of imaging the low levels of fluorescence emitted from large specimens. For the most extreme low light conditions, the present invention incorporates an optional light amplification system that may be inserted between the lens and the CCD camera (see below).

Lens Subassembly

FIG. 2 shows the general arrangement of illumination and filter components within the telecentric lens 22. The lens has mounted within it a fiber optic ring light 44, which projects monochromatic illumination through the front lens element onto the specimen (leftward in FIG. 2). The focus plane of the ring light is at B, while the focus plane of the entire lens is in front of that point, at A. Placing the focus of the ring light at a point beyond the specimen minimizes specular reflections from the specimen.

The emission filter slot 62 allows insertion of an interference filter that removes excitation illumination from the incoming rays, leaving only the fluorescence emitted by the specimen.

FIG. 3 shows best the optical components of the telecentric, macro lens 22. The lens has 39 surfaces, and the following characteristics:

| Effective focal length | 164.436 mm |
|---|---|
| Numerical aperture | .443 |
| Magnification | 0.25 |

Note that light rays are almost parallel at the emission filter slot 62. This allows the filter to operate at its specified wavelength and bandwidth.

Although the present invention may be used with any lens, the highest sensitivity is available from its specially designed lens. This lens is fast, telecentric, and incorporates the epi-illumination system appropriate to large specimen formats.

Epi-illumination is a standard technology in fluorescence microscopy, where small areas are illuminated. The most efficient way to illuminate a small area is to place dichroic beam splitter behind the objective. A dichroic beam splitter or mirror is a partially reflective surface that reflects one wavelength range, while allowing another wavelength range to pass through.

On a microscope, illumination enters the dichroic mirror from the side. The mirror is angled to reflect the excitation light down through the objective toward the specimen. Fluorescence emitted by the specimen (shifted up in wavelength from excitation) is collected by the objective, which passes it upwards towards the dichroic mirror. The dichroic mirror is transparent to the emission wavelength, so that the light proceeds through the dichroic to the detector plane. A different dichroic is required for each excitation/emission wavelength.

There are major difficulties in applying the standard form of dichroic-based epi-illumination system to macro imaging.

a. The dichroic mirror must be at least as large as the objective it must fill. Camera lenses are much larger than microscope objectives, and would need correspondingly large dichroic mirrors. Dichroic mirrors this large are not readily available.

b. In a fast macro lens, it is critical that the back lens element be mounted as close as possible to the CCD. Any increase in the distance between the rearmost lens and the CCD markedly reduces the working f number and the light-gathering efficiency. Therefore, there is no room for a dichroic to be mounted behind the lens.

c. In a normal epi-illumination system, the dichroic reflects excitation through the entire lens. For this reason, transmission of excitation illumination is highly subject to the optical characteristics of the glasses used in the lens. Very costly (and difficult to work) quartz glass optics are required for UV epi-illumination. These UV-transparent optics can be constructed in the small sizes needed for a microscope objective, but would be astronomically expensive in the large sizes described for the present invention.

d. Dichroic beam splitters absorb light. Typically, they are 80–90% efficient.

A unique property of the present invention is that no dichroic is necessary. The telecentric lens is large, so there is room to install an illumination assembly within its body. The illuminator is mounted so that it shines directly at the front lens element, from behind. This illuminates the specimen, without any need of a reflective dichroic mirror. Any stray excitation illumination that is reflected back through the lens is removed by the emission barrier filter, located posterior to the illumination source.

Further, the lens is designed so that only one of the fifteen internal lens components resides in front of the internal illuminator. This has the advantage that internal flare and reflections are minimized. Of equal importance, only the front lens needs to be transparent to UV. A single UV-transparent lens is costly, but not prohibitively so.

The front element of the lens is calculated so as to focus the illumination source beyond the plane of the specimen. The defocus of the illumination source at the specimen plane minimizes reflections. As many well plates are constructed of polished plastic, and tend to generate specular reflections, this is an important feature.

The lens is highly efficient. The collection F/# of the lens is 4.5. This implies a collection solid angle of 0.03891 sr, and a collection efficiency of $0.03891/4p=0.3096\%$. The expected transmission value is 0.85–0.90, giving an overall collection efficiency of 0.263–0.279%. In comparison to an F/1.2 photographic lens, the expected improvement with the present lens is about 340%.

The present lens is telecentric. A telecentric lens is free of parallax error. Images of deep, narrow targets, made with standard lenses, exhibit parallax error. Circular targets at the center of the image are seen as true circles. However, the lens peers into lateral targets at an angle. Therefore, these lateral targets are seen as semilunar shapes. In many cases, one cannot see the bottom of a well at all. A telecentric lens collects parallel rays, over the entire area of a well plate. Thus, it does not peer into any wells at an angle and is free of parallax error.

A critical advantage of the present lens is that the internal beam is collimated at a position appropriate to the insertion of a barrier filter. That is, the lens is calculated so that rays are nearly parallel, at a point about midway in the lens barrel. The lens accepts an interference filter at this point. The filter serves to remove excitation illumination, and other nonspecific light. The collimated beam at this point is critical, because interference filters must be mounted orthogonal to the incoming illumination. If the incoming illumination is at an angle, the filter exhibits alterations in the wavelengths that it passes. In the present invention, light rays are almost parallel when they strike the filter, yielding the best possible performance.

The telecentric lens has a fixed field of view (about 14.5 cm diameter, in this case) but, if larger specimens need to be imaged, a motorized translation table may be mounted within the light-tight chamber. The translation table moves the specimen relative to the lens, under computer control. After each motion, a single "tile" is acquired. When the entire specimen has been imaged, all the tiles are recomposed (by the software) into a single large image, retaining telecentricity, freedom from parallax error, and high resolution over its entire surface.

Extreme Low Light Modification

Figure 4:
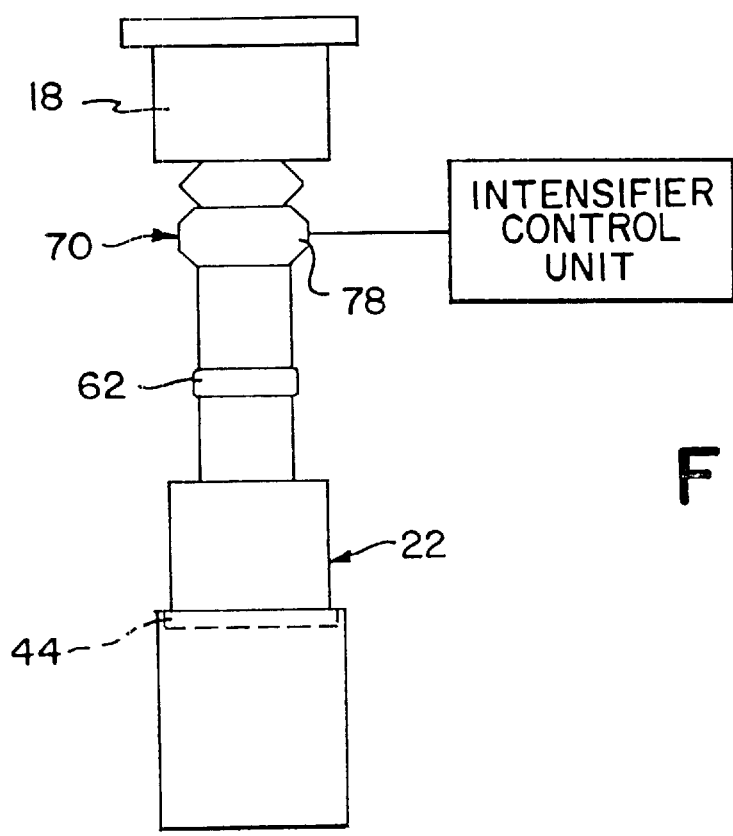
FIG. 4 is a schematic diagram illustrating a second embodiment of a system in accordance with the invention useful for extreme low light applications, which has an intensifier mounted between the lens and the CCD camera.

FIG. 4 shows a modification to system of FIG. 1, addition of an optional intensifier 70 to provide an alternate system useful for extreme low light imaging. In all other respects the system is essentially identical to that of FIG. 1. The intensifier 70 is mounted between the telecentric lens 22 and the CCD camera 18.

Figure 5:
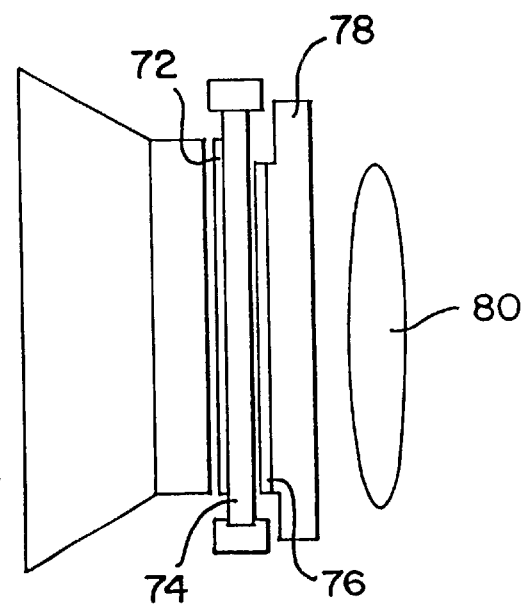
FIG. 5 is a schematic illustration of the intensifier.

FIG. 5 shows best the intensifier 70 as being of the GEN 3 type, and including a photosensitive cathode 72, a microchannel plate (MCP) 74, a phosphor screen 76, and a vacuum sealed body or enclosure 78. The fast, telecentric lens 22 (FIGS. 2,3) is placed in front of this assembly 70. At its output, the lens is focused on an input window of the cathode 72 so as to transfer the specimen image thereto. The photosensitive cathode 72 is selected to emit electrons in proportion to the intensity of light falling upon it. The MCP 74 is positioned within the vacuum sealed body 78, between the cathode 72, and the phosphor screen 76 and coupled to the cathode 72 at each end. The MCP 74 is provided with an array of small diameter MCP channels, each of which is coated with gallium arsenide. The electrons emitted from the cathode 72 are accelerated along the MCP channels to the phosphor screen 76. As the electrons from the cathode are accelerated along the small diameter channels, they strike the coated channel walls to produce additional electrons. As the multiplied electrons leave the MCP channels, they strike the phosphor screen 76 and produce an intensified image of the specimen on an output window. This image is coupled to the CCD 84 element in the camera by a lens 80.

It has been found that the use of the Extended Blue GEN 3 image intensifier is advantageous over other types of intensifiers in that the image provided on the output screen is sharper, has less shading error, and has less noise than those produced by GEN 1 and GEN 2 intensifiers. It is to be appreciated, however, that as better intensifier technologies are developed, they may be incorporated into the present system.

The integrating camera 18 is configured so that the highly amplified image generated on the output window 78 is focused by the intermediate lens 80 onto the CCD element 84. To image low light specimens, the CCD element 84 of camera 18 integrates for a period. During the integration period, photons from the output window incident to the CCD element 84 are stored as negative charges (the signal) in numerous discrete regions of the CCD element 84. The amount of charge in each discrete region of the CCD element 84 is accumulated as follows.

Signal=Incident light×Quantum efficiency×Integration time

The greater the relative intensity of the incident light coming from the intensifier 70, the greater the signal stored in the corresponding region of the CCD element 84.

For the most extreme low light conditions, as with the scintillation proximity assay, the present invention allows a light amplifier to be inserted between the lens and the CCD camera. In the preferred configuration, this light amplifier is an image intensifier. Intensification, as for example, is disclosed in U.S. Pat. No. 5,204,533 to Simonet, involves the coupling of an image intensifier to a CCD camera. The image intensifier typically includes a photocathode, a phosphor screen, and a microchannel plate (MCP) connected between the photocathode and phosphor screen. Light amplification factors of up to about 90,000 are possible with this type of device.

With the intensifier inserted into the optical chain, the present invention becomes an image intensified CCD (ICCD) camera. In an ICCD camera, the image is created at three or four planes. At each of these planes, there is some loss of quantum efficiency. Therefore, the image intensifier is operated at high gain to overcome signal losses within the optical chain. At very high gain factors, noise and ionic feedback through the MCP become so severe that further improvement of sensitivity is impossible. Even when run at maximum gain, conventional image intensified CCD cameras are not sensitive enough to image the dimmest specimens.

Faced with a typical very dim specimen, most ICCD cameras will fail to produce an image, or will produce a very poor image, in which the target will be difficult to discriminate from background, and the true range of target intensities will not be rendered. In the worst cases, the target will be indiscriminable from background.

Conventional image intensified CCD cameras use an integration period equal to a single television frame. The short integration period allows the intensifier to be used with standard, low-cost video cameras, as for example, are used in the television industry. In other cases, the intensifier is gated, to use very short integration periods (e.g. 1 msec). The use of gating allows the intensifier to be used in a photon counting mode.

The present invention offers two methods by which intensified light may be used. The preferred method involves continuous integration of the output of the intensifier onto a cooled CCD camera. This method is fast and efficient, but has limited dynamic range. Cooling of the intensifier, or multiple exposures for different times, may be used to improve the dynamic range. A second method involves looking at shorter periods of intensifier output, and photon counting. This method is much slower, but has broad dynamic range. The present invention allows either strategy to be selected, as warranted by the specimen.

Prior art exists for the use of intensified CCD cameras in well plate assay imaging. Martin and Bronstein (1994) and Roda et al. (1996) discuss use of an intensified CCD camera for the imaging of chemiluminescent specimens. Only bright specimens can be seen. No provisions are made for imaging deep wells without parallax error, or for applying monochromatic excitation to the specimen.

U.S. Pat. No. 4,922,092 (1990) to Rushbrooke et al. discloses the use of an image intensified CCD camera which is coupled to a special fibre optic lens. The fibre optic lens consists of bundles which transmit light between an array of wells and the input of the intensifier. While the invention disclosed by Rushbrooke is free of parallax, and may be suitable for standard 96 or 384 well plates, it would be incapable of imaging the very high density well arrays addressed by the present invention. Further, the invention disclosed by Rushbrooke lacks illumination capabilities. It is also incapable of imaging specimens in free format, because there is space between the input bundles that is not addressed. By using lens input, as opposed to fiber optics, the present invention allows free format imaging.

In sum, the present embodiment of the invention allows the use of an optional intensifier placed behind the lens, to detect the most extreme low light specimens. When intensified, the device can be run in continuous integration or photon counting modes.

With the system shown in FIGS. 4 and 5, only the CCD sensor is cooled. This is sufficient for most purposes. It is to be appreciated however, that the intensifier photocathode 72 could also be cooled, thereby improving the signal to noise ratio of the intensifier. Similarly, the entire photosensitive apparatus (intensifier+CCD) can be cooled. However, cooling the entire photosensitive apparatus has the disadvantage that the efficiency of the phosphor on the fibre optic output window is decreased.

Although a high quality, scientific grade CCD camera can detect about 50 photoelectrons incident to the CCD (depending on how we set reliability of detection), this is not an accurate indication of performance in imaging luminescent specimens. Real-world performance is complicated by the emission and collection properties of the entire optical chain, as well as by the performance of the CCD camera. Therefore, we need to go beyond the QE of the detector, and examine the transfer efficiency of the entire system.

Three factors dominate the transfer efficiency (photoelectrons generated/photons emitted) of the detector system. These are the light collection efficiency of the lens, the quantum efficiency of the CCD detector, and the lens transmittance. We can calculate the number of photoelectrons generated as follows:

$$Npe = \tau * \phi_{detector} * c.e. * N_{photons}$$

where

| | | |
|---|---|---|
| $\tau$ | is | lens transmittance, about 85–90% for our lens |
| $\phi$ | is | quantum efficiency of the CCD detector, typically about 35–40%, up to 80% in our case, and |
| c.e. | is | collection efficiency of lens, less than .1% for fast photographic lenses, about 1.2% in our case. |

In a typical scientific grade CCD camera system, using the fastest available photographic lens (f1.2), and with a high quality cooled detector, the CCD will generate 1 photoelectron for about 5,000–10,000 photons generated from a point source in the sample.

The lens of the present invention offers a collection efficiency of about 0.271%. The efficiency of the CCD detector is about double that of other CCDs. The result is that the present invention has the theoretical ability to generate one photoelectron for about 500–1000 photons generated from a point source within the sample. This very high transfer efficiency allows detection of specimens that cannot be imaged with prior art systems.

In the alternate embodiment of the invention shown in FIGS. 4 and 5, the system incorporates an extended blue type of GEN 3 image intensifier. Other types of intensifiers, although less preferred, may also be used. The three major types of intensifier (GEN 1, GEN 2 and GEN 3) differ in the organization of their components and in the materials of which the components are constructed. In a GEN 1 intensifier, illumination incident to a photocathode results in emissions at a rate proportional to the intensity of the incident signal. The electrons emitted from the photocathode are than accelerated through a high potential electric field, and focused onto a phosphor screen using electrostatic or proximity focusing. The phosphor screen can be the input window to a video camera (as in the silicon intensified target camera), or can be viewed directly. GEN 1 intensifiers suffer from bothersome geometric distortion, and have relatively low quantum efficiency (about 10%).

The GEN 2 intensifiers, like the GEN 3, incorporate a MCP into an image tube, between the cathode and an anode. The GEN 2 intensifiers are smaller, lower in noise, and have higher gain than the GEN 1 intensifiers. However their quantum efficiency is fairly low (typically <20%), and they tend to suffer from poor contrast transfer characteristics. In contrast, the GEN 3 intensifier tube has a quantum efficiency of about 30% or higher (needs less gain), and very high intrinsic contrast transfer. With recent versions of the GEN 3, gain levels are about equal to those of a GEN 2 (ultimate gain level available is about 90,000). Therefore, a GEN 3 intensifier will tend to yield better images than a GEN 2. Where necessary for reasons of cost or specific design features, other forms of intensifier could be used. Similarly devices with high intrinsic gain (such as electron bombarded back-illuminated CCD sensors) could be used in place of image intensifiers.

The CCD camera 18 of the present invention could use integration periods locked to a gated power supply in the image intensifier, with the result that the camera could be read out at very short intervals. Using the gating and fast readout feature, and with the intensifier run at highest gain or with a multistage intensifier, the present invention can thereby be operated as a conventional photon counting camera. Thus, the present system can advantageously be used for both direct imaging of faint specimens, or as a photon counting camera by changing its mode of operation from integration to gating.

CCD Camera System

Figure 8:
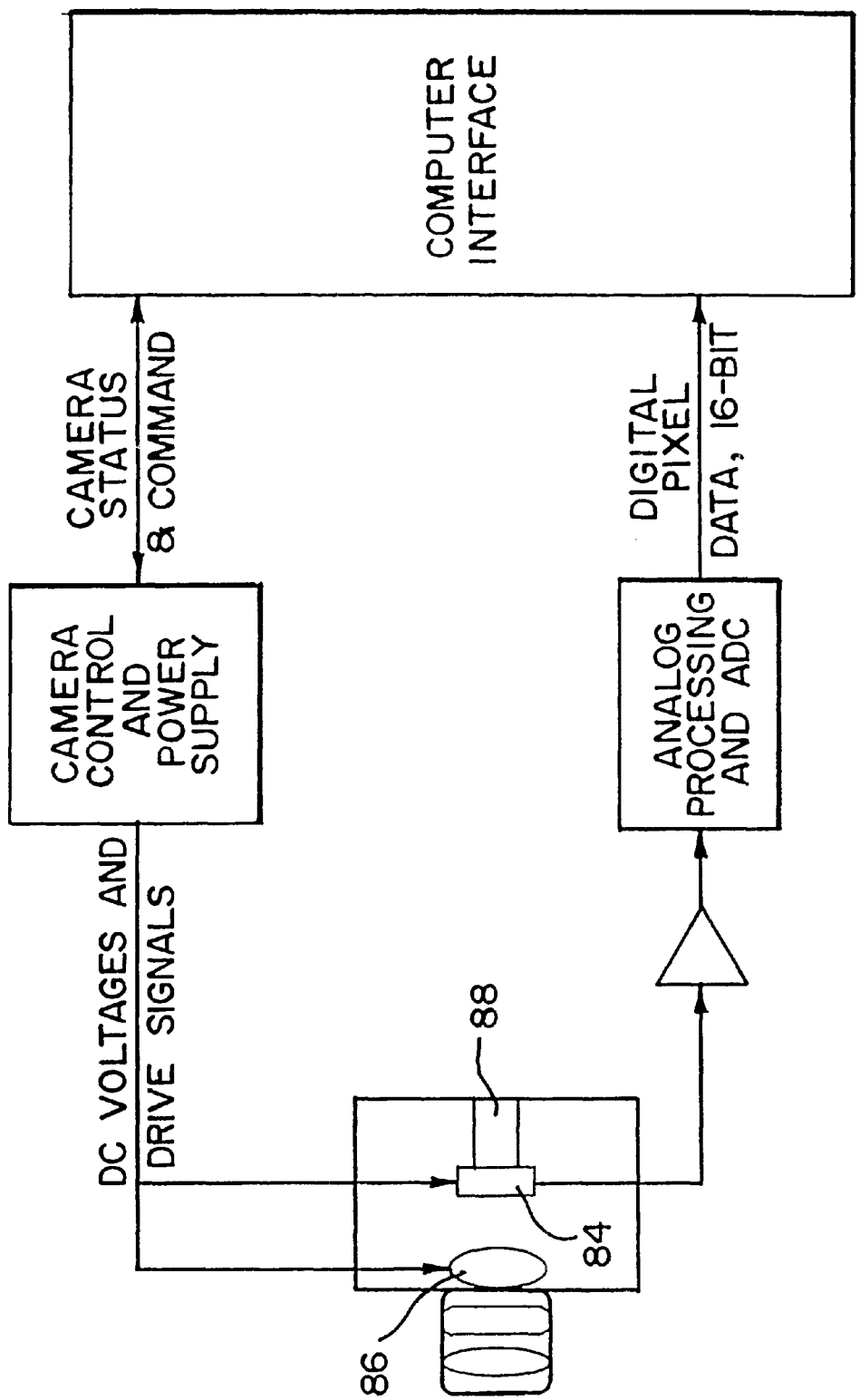
FIG. 8 is schematic diagram of the CCD camera.

FIG. 8 is a schematic representation of the CCD camera 18. The camera 18 includes a CCD element 84 positioned behind a camera aperture. To reduce dark noise produced by electrons within the CCD, the CCD element 84 is mounted to a heat sink 88, which in turn is thermally coupled to a Peltier cooling element and liquid circulation system for providing enhanced heat dissipation. The lens is positioned over the aperture to focus the image on the CCD element 84. The fast, telecentric lens 22 (FIGS. 2 and 3) is mounted directly to the camera body by screws, after removing the photographic lens mount. Similarly, the image intensifier 70 (when present) is mounted directly to the camera body.

Area imaging systems use CCD arrays to form images. Factors which influence the ability of CCD arrays to detect small numbers of incoming photons include quantum efficiency, readout noise, dark noise, and the small size of most imaging arrays (e.g. 2.25 cm$^2$).

Quantum efficiency (QE) describes the ability of the photodetector to convert incident photons into electron hole pairs in the CCD. Consumer-grade CCDs typically exhibit QE of about 12–15%. Standard, scientific grade cooled CCD cameras exhibit QE of about 40%. A very limited number of thinned, back-illuminated CCDs can achieve QE of as high as 80% at peak detection wavelengths.

Readout noise originates in the output preamplifier of the CCD, which measures the small changes in voltage produced each time the charge content of one or more CCD elements is transferred to it. Readout noise is directly related to the readout rate, and is decreased by use of slow readout.

Dark noise is produced by thermally generated charges in the CCD. By increasing the background level, dark noise decreases dynamic range. The constant dark noise level can be subtracted from the image, but dark noise also has a random noise component which cannot be subtracted. This component adds to the noise level of the detector. Dark noise is decreased by cooling the CCD.

The size of the CCD element is related to its ability to store photoelectrons (known as the well capacity) and, hence, its dynamic range. The larger each CCD element in the array, the larger the full well capacity and dynamic range of that element. A broad dynamic range allows the detector to be used for longer exposure times, without saturation, and this enhances the detection of very small signals. Further, the signal to noise performance of larger elements is inherently higher than that of smaller elements. Most area imaging systems use relatively small CCDs. This results in limited resolution for devices in which the discrete CCD elements are large, and limited dynamic range for devices in which the discrete CCD elements are small. Devices with limited dynamic range cannot achieve 16 bit precision, and must be used with relatively bright specimens (e.g. fluorescence microscopy, UV gels, very bright chemiluminescence).

The present invention incorporates a CCD system which is designed to minimize all of the problems just described. The CCD array is unusually large (6.25 cm$^2$) and efficient (about 80% quantum efficient). The result is very high detector sensitivity with broad dynamic range (true 16 bit). The preferred support electronics include a high-precision digitizer, with minimal readout noise. Preferably, the camera is cooled to minimize dark noise.

An electro-mechanical shutter mechanism is additionally provided within the camera, for limiting the exposure of the image on the CCD element. Preferably the camera is a thinned, back-illuminated 1024×1024 pixel black and white camera with asynchronous reset capability, and high quantum efficiency. The camera provides a 16-bit digital signal output via digitization circuitry mounted within the camera control unit, and an interface card mounted within the computer. Data from the CCD are digitized by the camera control unit at the rate of 200,000 pixels/second, and transferred directly to the computer memory.

Following the integration period, the CCD camera accepts a trigger pulse from the computer to initiate closure of the electromechanical shutter. With the shutter closed, the image is transferred from the CCD to the internal frame buffer of the computer.

Although this camera could be used without cooling the CCD element, extended periods of integration are achieved by using a CCD camera with an integral cooling element. The effectiveness of integration is limited by the degree of cooling. With a non-refrigerated liquid cooling device, sensor temperatures of about −50° C. (below ambient) can be achieved. At this temperature, dark noise accumulates at a rate of about 7–10 electrons/second. This type of cooling has the advantage of low cost and easy implementation.

It is to be appreciated, however, that longer periods of integration are possible if refrigerated liquid or cryogenic cooling are employed.

Control Subsystem

The control subsystem 16 comprises, control unit 26 and computer 28. Camera control unit is a computer controllable unit provided by the manufacturer of camera 18 to control the camera. Computer 28 is preferably a conventional computer running in the Windows® environment and is programmed to achieve image acquisition and analysis in accordance with the present invention.

Camera-based imaging systems lack the sort of push-button operation that is typical of counting or scanning systems. Focusing the camera, adjusting exposure time, and so forth, can all be inconvenient.

In fact, imaging is inherently more complex than counting single targets within wells. Nonimaging counting systems have a relatively easy task. They only need to control the scanning process, control internal calibration, and create a small array of data points representing each well. The sequence of steps might be as follows.

a. Calibrate detector against internal standard.
b. Illuminate one well.
c. Position a PMT over the illuminated well.
d. Read well.
e. Transfer data to spreadsheet.
f. Illuminate next well and repeat.

An area imaging system has a much more difficult task. Imaging a well plate might include the following requirements.

a. Provide adequate illumination over the entire plate.
b. Control a high performance camera.
c. Store geometric and density correction factors.
d. Image specimen.
e. Correct geometric and density variation.
f. If necessary, calibrate image to standards within the specimen.
g. Locate each well and quantify intensity.
h. Transfer data to spreadsheet.

These tasks can only be performed if the imaging system is equipped with software that performs functions b–h, above. The present invention incorporates such software.

In particular, one aspect of the present invention is software which corrects for nonspecific background fluorescence by using two images. The first image is made with an excitation filter that excites as little specific fluorescence as possible, while exciting nonspecific fluorescence. The second image is made with an excitation filter that excites specific fluorescence as much as possible, and as little nonspecific fluorescence as possible. An optimal specific fluorescence image is made by subtracting the nonspecific image from the specific image.

Figure 9A:
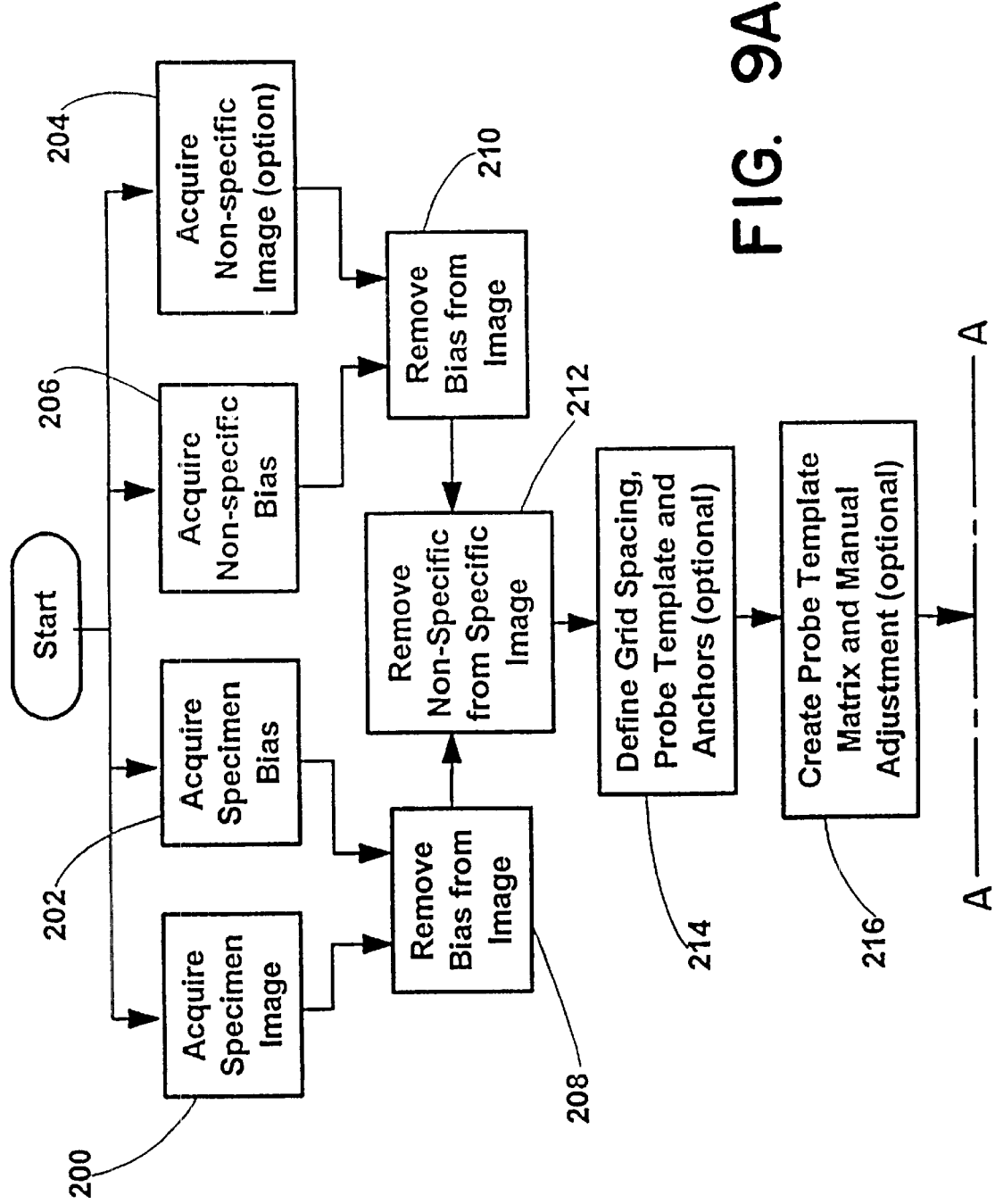
FIGS. 9A and 9B, collectively referred to below as FIG. 9, represent a flow chart illustrating the method utilized for image acquisition and analysis in accordance with the present invention.
Figure 9B:
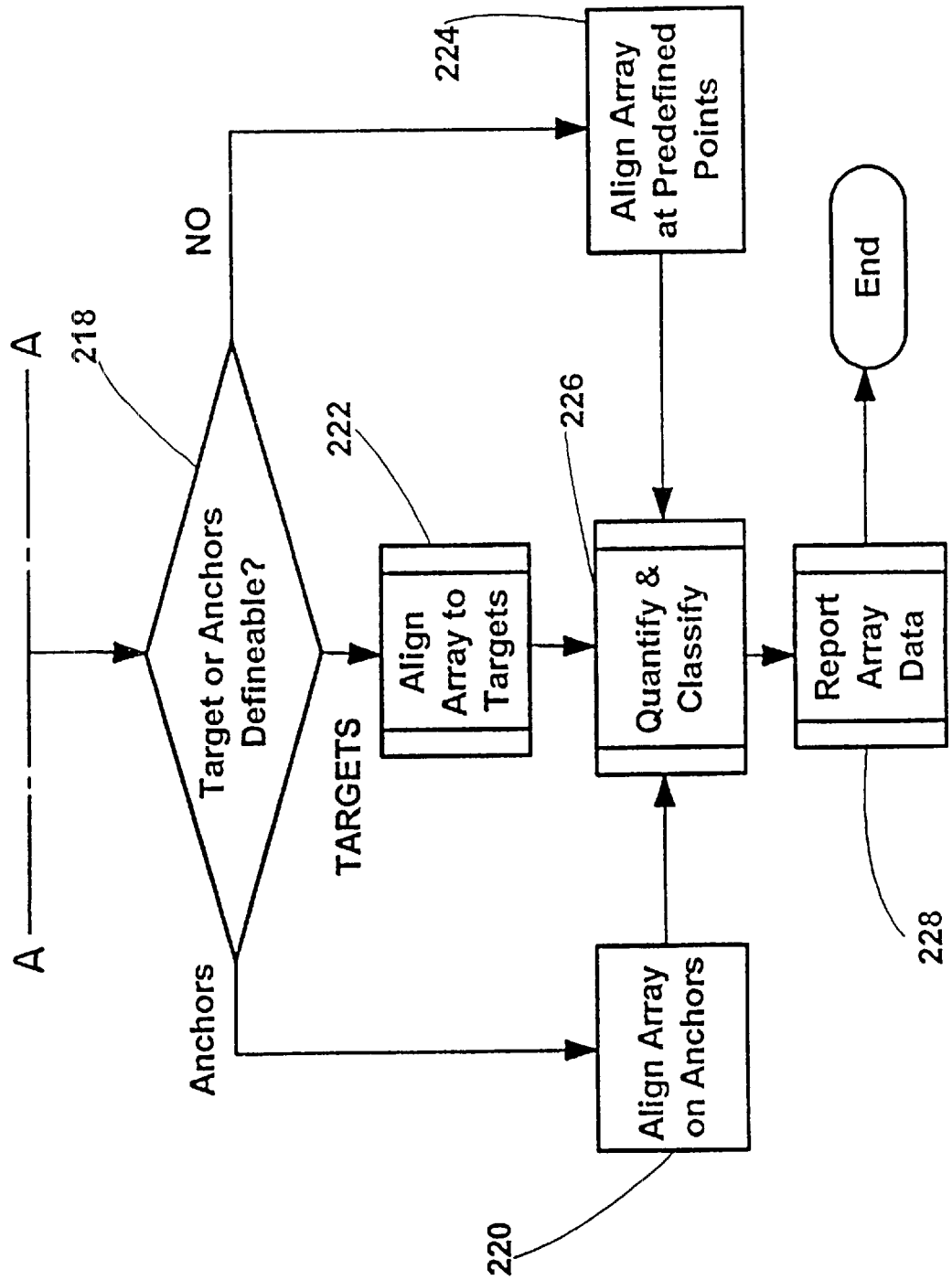

FIG. 9 is a flow chart illustrating the primary process performed by computer 28 in controlling the system 1 and acquiring data therefrom. After initiation of the process, an image of the specimen is acquired at block 200 using camera 18. Known processes exist for acquiring bias images of a specimen. Such bias images take into account all significant distortions and errors introduced by the system itself when an image is taken. Utilizing one of the known methods, a bias image for the specimen is acquired at step 202.

At Step 204, a non-specific image is acquired. This image determines the contribution of non-specimen components, such as the support substrate, to the image. This step is indicated as optional, since it would only be performed in the event that the specimen had to be illuminated in order to acquire the specimen image, in which event some light would also be reflected from non-specimen elements. On the other hand, if the specimen were the source of the light for the image (as in chemiluminescence), the non-specific image would not be acquired. Similarly, the step at block 206 is optional, since it involves obtaining a non-specific bias image.

At block 208, the specimen bias image is removed or subtracted from the specimen image, and at block 210 the non-specific bias image is subtracted from the non-specific image. This results in two images in which bias effects have been compensated. At step 212, the compensated non-specific image is removed from the compensated specimen image to produce a working image in which the effects of the specimen are isolated. Those skilled in the art will appreciate that if steps 204 and 206 were not performed, steps 210 and 212 would also not be performed.

Following bias removal, various other corrections are provided (e.g. for geometric warping originating in the lens), using known processes.

At step 214, the operator inputs to the computer the nominal "grid" spacing and "probe template". The grid spacing is the nominal center-to-center spacing of specimen samples on the substrate. The "probe template" is the nominal definition of a single target (e.g. in terms of shape and area) corresponding to one dot on a membrane, one well in a plate, or similar target. Typically the probe template is a circular area, and there is one probe template for each target in the specimen. A grid is composed of a matrix containing one probe template for each of the targets.

Optionally, the operator can also define an array of "anchor points." The specimen may include an array of thousands of potential samples. In some instances, a large proportion of these will be populated, and in others relatively few will. In those instances in which relatively few sample points are populated, the specimen will include predefined "anchor" points to aid the system locating the probe template positions. In those instances in which a large proportion of the potential sample sites are populated, the samples themselves provide a sufficient population to position the probe templates, and anchor points may be unnecessary.

At block 216, probe templates of the defined size with the defined grid spacing are generated and superimposed over the working specimen image. At this point, the operator can optionally provide a manual adjustment to the superimposed grid of probe templates, in order to bring them into general alignment with the actual specimens. He could do so, for example, by utilizing a mouse to shift the entire array then "grab specific probe templates and center them over the appropriate targets on the specimen. The operator might, for example, perform a general alignment by centering the probe templates in the four corners of the grid over the appropriate targets of the specimen. Although not essential, this manual adjustment will speed and simplify the processing done by computer 28.

At block 218, a process is performed, described in more detail below, in order to determine more precise locations for the probe templates relative to the actual location of potential targets. At the outset of this process, at block 218, a determination is made whether the targets or anchor points have been adequately identified or defined. If targets have been well-defined, control is transferred to block 222, where the array of probe templates is aligned to the defined targets; if not, but anchors have been well-defined, control is transferred to block 220, where the array of probe templates is aligned to the anchors; otherwise, control is transferred to block 224, where the predefined grid spacing and probe template for the array are utilized. It will be appreciated that, in some instances, it may be desirable to align the array on anchors and then on targets.

Once the probe templates and targets are aligned, the measurements within the individual probe templates are decoded to different conditions. For example, a probe may be capable of assuming any of n conditions, and the process of block 226 could decode the sample at each probe to one of those conditions. The actual process is performed on a statistical basis, and is best understood from a simple example relating to resolving a binary decision. However, those skilled in the art will appreciate that the process could actually be applied to resolving a multiple condition process. In the simplest case, the binary decision is a "yes" or "no" decision, which could be related to the presence or absence of a certain condition. In accordance with the process at block 226, the actual levels at every probe of the specimen are measured, a mean and standard deviation are determined for the set of samples, and this results in a working statistical distribution. The decoding of a "yes" or "no" could then be done to any level of confidence selected by the operator. The operator's selection of a level of confidence results in the determination of a threshold level (e.g. based upon that level being located a calculated number of standard deviations from the mean on the distribution curve), and any signal above the threshold level would be considered a "yes", while any signal below the threshold level would be considered a "no."

At block 228, a process is performed to generate a report of the array data, based upon the process performed at block 226. It is contemplated that this may be any form of report writing software which provides the operator a substantial amount of flexibility in preparing reports of a desired format. Once the reports are generated, the process ends.

Attached as Appendix A is a more detailed discussion of the process of FIG. 9.

Figure 10:
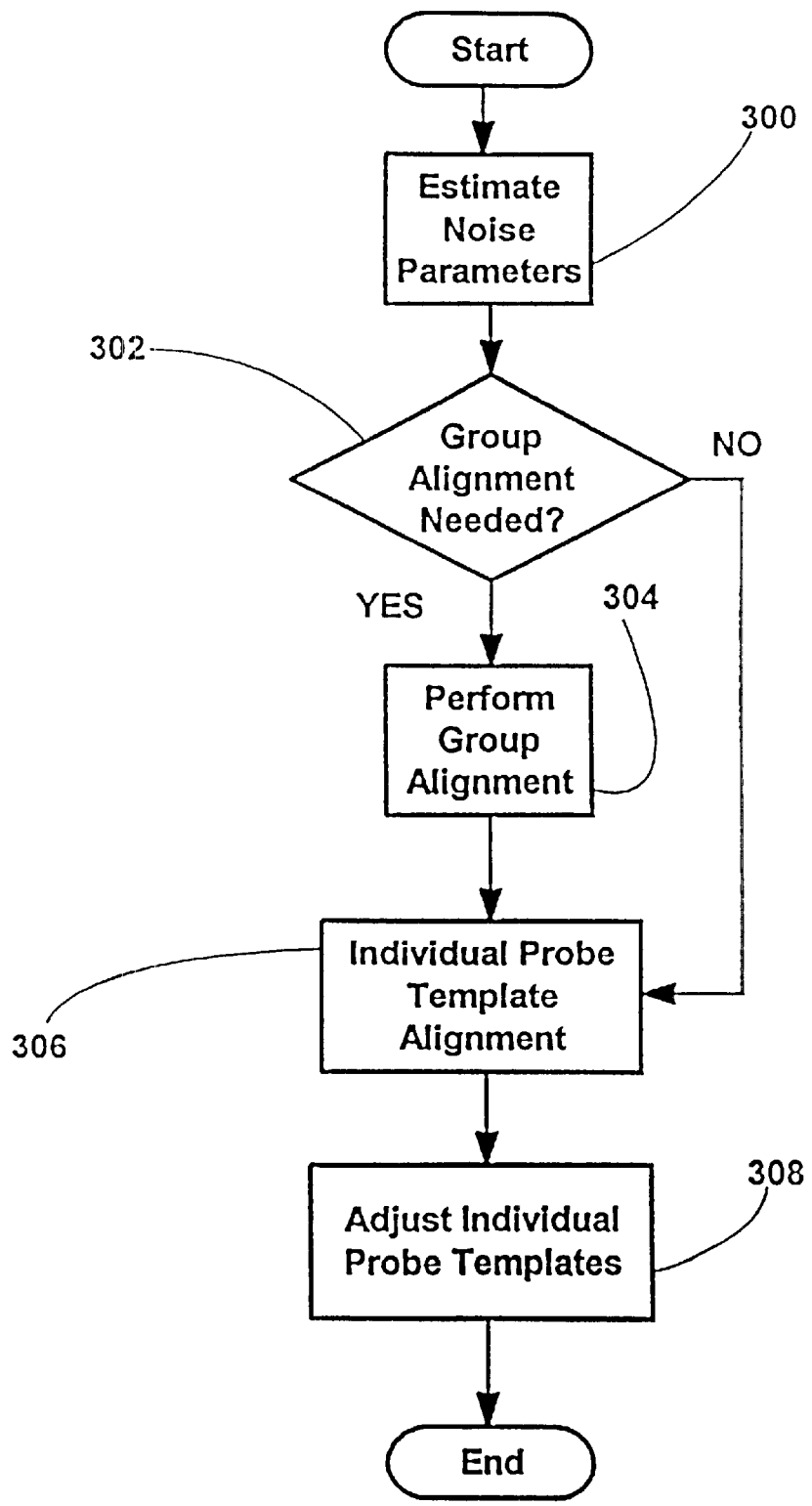
FIG. 10 is a flow chart illustrating the method utilized for locating targets in the process of FIG. 9.

FIG. 10 is a flow chart illustrating the process performed in block 222 of FIG. 9.

After initiation of the process, image background and noise are estimated at block 300. At block 302, a determination is made whether a group alignment of the grid to the array of targets is necessary. This could be done either visually by an operator or by the system. The purpose of this test is to determine whether the grid is aligned to the targets overall. If done by the system, it would be performed by a conventional procedure for testing alignment of two regular patterns of shapes. If it is determined that adequate alignment of the group exists, control is transferred to block 306.

At block 304, a group alignment is performed. The purpose of this operation is to align the probe template grid roughly with the respective targets. The alignment may be done on the basis of the whole grid or part of the grid selected by the operator. This alignment could be done by the process discussed below with respect to block 306 for maximizing ID, except that ID is maximized over the entire grid.

At block 306, a step-wise process is performed within the area of each individual probe template to locate that point which yields the maximum integrated density, ID, within the probe template, given by the formula (1):

$$ID(x0, y0) = \int_{S(x0, y0)} D(x, y) W(x-x0, y-y0) dx dy \qquad (1)$$

where:
(x0,y0) is the center point of a probe template;
S(x0,y0) is the probe template area at (x0,y0);
D(x,y) is the density value (e.g. brighteners) at (x,y); and
W(x,y) is a weighting function (e.g. a two-dimensional Gaussian function with its maximum value at (0,0)).

This yields an "A location" for each probe template, which is that location that provides the maximum value in formula (1). The probe template location prior to block 306 will be referred to as the "G location."

At block 308, a confidence weighting is performed between the A location and G location, in order to arrive at the final location of the center of each probe template. The confidence weighting factor for each A location is a form of signal-to-noise ratio. That is, the value of ID at each point is proportional to the ratio between the ID value at that point and the value determined at block 300 for that point. In effect the weighting factors are utilized to determine the position of the probe center along a straight line between the A and G locations, with weighting determining how close the point is to the A location.

Although the detailed description describes and illustrates preferred embodiments of the present apparatus, the invention is not so limited. Modifications and variations will now appear to persons skilled in this art. For a definition of the invention reference may be had to the appended claims.

What is claimed is:

1. A system for imaging assays in a multi-sample plate having at least one sample in a recessed well, the plate being positioned to have light incident thereon or originating from a sample, comprising: a telecentric lens suitable for imaging said multi-well plate positioned to collect light from said plate, the collection of light from said at least one sample being improved owing to the ability of the telecentric lens to peer into the well, the collected light being transmitted through said telecentric lens; and an image detection device positioned to receive light transmitted through said telecentric lens and to produce a signal representing an image of the plate.

2. The system of claim 1, wherein said image detection device is a CCD camera.

3. The system of claim 2 wherein said plate has wells to contain said samples.

4. The system of claim 1 wherein said plate has wells to contain said samples.

5. A system for imaging assays in a multi-sample plate having at least one sample in a recessed well, the plate being positioned to have light incident thereon or originating from a sample, comprising: telecentric lens means for peering into the well of said at least one sample in order to improve the collection of light therefrom, the light collected by said telecentric lens means being transmitted therethrough; and an image detection device positioned to receive light transmitted through said telecentric lens means and to produce a signal representing an image of said at least one sample.

* * * * *